(12) United States Patent
Kim et al.

(10) Patent No.: US 12,427,098 B2
(45) Date of Patent: Sep. 30, 2025

(54) COMPOSITION FOR HAIR TREATMENT, CONTAINING OLEFIN-BASED UNSATURATED HYDROCARBON-CONTAINING OIL

(71) Applicant: LG HOUSEHOLD & HEALTH CARE LTD., Seoul (KR)

(72) Inventors: Joong-Hun Kim, Seoul (KR); Sang-Hun Song, Seoul (KR); Seong-Kil Son, Seoul (KR); Yoo-Jung Seo, Seoul (KR); Byung-Tack Lim, Seoul (KR)

(73) Assignee: LG HOUSEHOLD & HEALTH CARE LTD., Seoul (KR)

( * ) Notice: Subject to any disclaimer, the term of this patent is extended or adjusted under 35 U.S.C. 154(b) by 630 days.

(21) Appl. No.: 17/776,866

(22) PCT Filed: Oct. 22, 2020

(86) PCT No.: PCT/KR2020/014521
§ 371 (c)(1),
(2) Date: May 13, 2022

(87) PCT Pub. No.: WO2021/096093
PCT Pub. Date: May 20, 2021

(65) Prior Publication Data
US 2022/0409503 A1 Dec. 29, 2022

(30) Foreign Application Priority Data

Nov. 15, 2019 (KR) .................. 10-2019-0146448
Nov. 15, 2019 (KR) .................. 10-2019-0146449

(51) Int. Cl.
*A61K 8/31* (2006.01)
*A61K 8/04* (2006.01)
(Continued)

(52) U.S. Cl.
CPC .............. *A61K 8/31* (2013.01); *A61K 8/042* (2013.01); *A61K 8/22* (2013.01); *A61K 8/922* (2013.01);
(Continued)

(58) Field of Classification Search
CPC . A61K 8/31; A61K 8/042; A61K 8/22; A61K 8/922; A61K 2800/4322;
(Continued)

(56) References Cited

U.S. PATENT DOCUMENTS 6,383,232 B1 * 5/2002 Wohlman ............... A61Q 5/12
 8/408
2003/0086882 A1 * 5/2003 Schmenger .......... A61K 8/044
 424/62
(Continued)

FOREIGN PATENT DOCUMENTS

DE 102010002863 A1 * 9/2011 ............. A61K 8/922
FR 2 672 491 A1 8/1992
(Continued)

OTHER PUBLICATIONS

Hirobe, T. (Biol. Pharm. Bull. 2009;32(8):1347-1353). (Year: 2009).*
(Continued)

*Primary Examiner* — Ernst V Arnold
(74) *Attorney, Agent, or Firm* — Birch, Stewart, Kolasch & Birch, LLP (57) ABSTRACT

The present disclosure provides a composition for hair and fiber treatment which supplies a transition metal as a catalyst to a thiol residue formed when hair or fiber is damaged in a process of chemical or physical care, and rapidly and abundantly binds an olefin-based unsaturated hydrocarbon through a thiol-ene reaction, thereby continuously providing smoothness to the hair and fiber.

14 Claims, 2 Drawing Sheets
(2 of 2 Drawing Sheet(s) Filed in Color)

(51) Int. Cl.
    *A61K 8/22*     (2006.01)
    *A61K 8/92*     (2006.01)
    *A61Q 5/00*     (2006.01)
    *A61Q 5/02*     (2006.01)
    *B01J 23/72*     (2006.01)
    *B01J 23/745*     (2006.01)

(52) U.S. Cl.
    CPC .............. *A61Q 5/002* (2013.01); *A61Q 5/02* (2013.01); *B01J 23/72* (2013.01); *B01J 23/745* (2013.01); *A61K 2800/4322* (2013.01)

(58) Field of Classification Search
    CPC . A61K 8/19; A61Q 5/002; A61Q 5/02; A61Q 5/004; A61Q 5/12; B01J 23/72; B01J 23/745; B01J 27/122; B01J 27/128
    See application file for complete search history.

(56) References Cited

U.S. PATENT DOCUMENTS

| | | |
|---|---|---|
| 2003/0152540 A1 | 8/2003 | Putman et al. |
| 2003/0185785 A1 | 10/2003 | Moyal |
| 2005/0076457 A1* | 4/2005 | Plos .................. A61Q 5/08 8/405 |
| 2009/0149361 A1* | 6/2009 | Adkison ............... A61Q 5/02 510/130 |
| 2013/0305463 A1 | 11/2013 | Uellner et al. |
| 2014/0353200 A1 | 12/2014 | Samain et al. |
| 2019/0240130 A1 | 8/2019 | Gregolin et al. |
| 2021/0015732 A1 | 1/2021 | Yoo et al. |

FOREIGN PATENT DOCUMENTS

| | | | |
|---|---|---|---|
| KR | 10-2004-0035235 A | 4/2004 | |
| KR | 10-2013-0101822 A | 9/2013 | |
| KR | 10-2018-0057932 A | 5/2018 | |
| KR | 10-2019-0068694 A | 8/2019 | |
| KR | 10-2019-0113069 A | 10/2019 | |
| WO | WO-02069921 A1 * | 9/2002 | .............. A61K 8/23 |
| WO | WO-03015734 A2 * | 2/2003 | .............. A61K 8/97 |

OTHER PUBLICATIONS

English translation of Battermann et al. (DE 102010002863); 2011; 24 pages. (Year: 2011).*

Al-Bachir et al., "Fatty acid profile of olive oil extracted from irradiated and non-irradiated olive fruits", International Journal of Food Properties, vol. 20, No. 11, 2017, pp. 2550-2558.

International Search Report (PCT/ISA/210) issued in PCT/KR2020/014521, dated Mar. 22, 2021.

Alfaparf Repair Shampoo, CosDNA, https://www.cosdna.com/chs/cosmetic_cbd2230253.html, Apr. 19, 2016, p. 1-5 (10 pages total), with English translation.

* cited by examiner

| Sample classification | Treatment | IR Image $\nu 2 = 1072\ cm^{-1}$ (scale= 10 μm) |
|---|---|---|
| #1 | Non-treatment |  |
| #2 | Damaged hair |  |
| #3 | Olive oil |  |
| #4 | Olive oil + Cu (monovalent) addition (Chloride) |  |
| #5 | Olive oil + Cu (divalent) addition (Chloride) |  |
| #6 | Olive oil + Cu (trivalent) addition (Chloride) |  | ns
COMPOSITION FOR HAIR TREATMENT, CONTAINING OLEFIN-BASED UNSATURATED HYDROCARBON-CONTAINING OIL

TECHNICAL FIELD

The present application claims the priority based on Korean Patent Application No. 10-2019-0146448 filed on Nov. 15, 2019 and Korean Patent Application No. 10-2019-0146449 filed on Nov. 15, 2019, and the entire contents disclosed in the description and drawings of the corresponding applications are incorporated herein by reference.

The present disclosure relates to a composition for hair treatment comprising an oil comprising olefin-based unsaturated hydrocarbon.

BACKGROUND ART

Hair cosmetics are also used for additional purposes such as ease of combing, giving softness, smoothness or gloss to hair, reduction of friction on the hair surface, prevention of static electricity or hair protection, or the like, in addition to having a hair-washing function to remove contamination from scalp and hair and keep hair clean and beautiful. Recently, there is an increasing demand for hair dyes, bleaching agents or perm agents that change hair color or shape for cosmetic purposes.

Hair dyes change the hair color by penetrating the dye component into the cortex by adjusting the pH to open and close the cuticle. In this process, disulfide of protein is destroyed to form cysteic acid or cysteine, but even if it is restored to acidity, the remaining part is 20%-30% or more, which leaves damage such as loss of smoothness to the hair.

As a study to overcome this, there have been methods of inhibiting formation of cysteine by introducing a specific molecule in a form of an amide (EP 2417964 A1), or applying oil to provide smoothness without significantly affecting the oxidative power. However, these have disadvantages in that they reduce the beauty function of the prior art, or give a sticky feeling of use due to temporary application, thereby reducing satisfaction due to discomfort.

Numerous documents are referenced throughout the present description, and citations thereof are indicated. The disclosure of the cited documents are incorporated herein by reference in their entirety to more clearly describe the level of the art to which the present disclosure pertains and the content of the present disclosure.

DISCLOSURE

Technical Problem

The present disclosure relates to a composition for hair treatment which contains a metal catalyst and an oxidation initiator, to activate a thiol-ene reaction and protect and recover oxidized hair, thereby adding a high conditioning effect.

Therefore, an object of the present disclosure provides smoothness to hair continuously by rapidly and abundantly binding an oil comprising olefin-based unsaturated hydrocarbon into a thiol residue formed by damaged hair or fiber in a chemical or physical care process through a thiol-ene reaction.

Another object of the present disclosure is to provide a composition for hair or protein-based fiber treatment containing the function.

Other object of the present disclosure is to provide a composition for hair treatment, particularly, a hair dye composition, containing the function.

Other object of the present disclosure is to provide a hair product and a fiber treatment product containing the function.

More specifically, an object of the present disclosure is to provide the following embodiments.

Embodiment A1. A composition for hair treatment, comprising a transition metal catalyst and an oil comprising olefin-based unsaturated hydrocarbon.

Embodiment A2. The composition for hair treatment according to Embodiment A1, wherein the composition has an effect of hair protection, hair recovery, giving conditioning feeling or prevention of hair oxidation.

Embodiment A3. The composition for hair treatment according to any one of the preceding embodiments, wherein the transition metal catalyst is one or more selected from the group consisting of monovalent transition metals, divalent transition metals, and salts thereof.

Embodiment A4. The composition for hair treatment according to any one of the preceding embodiments, wherein the transition metal catalyst is one or more selected from the group consisting of copper salts and iron salts.

Embodiment A5. The composition for hair treatment according to any one of the preceding embodiments, wherein the olefin-based unsaturated hydrocarbon is a C6 to C22 fatty acid comprising at least one unsaturated group.

Embodiment A6. The composition for hair treatment according to any one of the preceding embodiments, wherein the transition metal catalyst facilitates a thiol-ene reaction between cysteine present in hair and the oil comprising olefin-based unsaturated hydrocarbon.

Embodiment A7. A hair product comprising the composition for hair treatment according to any one of the preceding embodiments.

Embodiment A8. The hair product according to Embodiment A7, wherein the hair product is selected from the group consisting of bleaching agents, dyes, perm agents, hair treatment agents, hair clinic agents, hair nutrition agents, hair care agents, hair cleaning agents, shampoos, conditioners, hair tonics, hair conditioners, hair lotions, hair gels, hair packs, hair cream, hair essence, hair powder, hair spray, hair oil, hair styling agents, patches, spray and post-dye treatment agents.

Embodiment A9. A composition for protein-based fiber treatment, comprising a transition metal catalyst and an oil comprising olefin-based unsaturated hydrocarbon.

Embodiment A10. The composition for protein-based fiber treatment according to Embodiment A9, wherein the transition metal catalyst facilitates a thiol-ene reaction between cysteine present in protein-based fiber and the oil comprising olefin-based unsaturated hydrocarbon.

Embodiment B1. A composition for hair treatment comprising (i) an oxidation initiator and (ii) an oil comprising olefin-based unsaturated hydrocarbon.

Embodiment B2. The composition for hair treatment according to Embodiment B1, further comprising an oxidation dye.

Embodiment B3. The composition for hair treatment according to any one of the preceding embodiments, wherein the oxidation dye is one or more selected from the group consisting of phenylene diamine, aminophenol, resorcinol, aminocresol, methylhydroxyethylaminophenol, nitrophenylene diamine and toluene diamine sulfate.

Embodiment B4. The composition for hair treatment according to any one of the preceding embodiments, wherein the oxidation initiator is one or more selected from the group consisting of hydrogen peroxide, sodium perborate, sodium percarbonate, ammonium persulfate, bis maleimidoethoxy ethane, calcium peroxide, ferric chloride, hypochlorous acid, laccase, magnesium peroxide, MEK (methyl ethyl ketone) peroxide, melanin peroxide, ozonized turpentine, phthalimidoperoxycaproic acid, potassium bromate, potassium caroate, potassium chlorate, potassium monopersulfate, potassium persulfate, PVP-hydrogen peroxide, sodium bromate, sodium carbonate peroxide, sodium iodate, sodium perborate, sodium persulfate, strontium peroxide, urea peroxide and zinc peroxide.

Embodiment B5. The composition for hair treatment according to any one of the preceding embodiments, wherein the olefin-based unsaturated hydrocarbon is a unsaturated fatty acid.

Embodiment B6. The composition for hair treatment according to any one of the preceding embodiments, wherein the oil comprising olefin-based unsaturated hydrocarbon comprises an unsaturated fatty acid of 50% by weight or more.

Embodiment B7. The composition for hair treatment according to any one of the preceding embodiments, wherein the oil comprising olefin-based unsaturated hydrocarbon is one or more selected from the group consisting of olive oil, macadamia oil, jojoba oil, meadowfoam oil, argan oil, camelia oil, grape seed oil, sunflower oil, avocado oil, canola oil, corn oil, cottonseed oil, hempseed oil, flaxseed oil, linseed oil, palm oil, peanut oil, safflower oil and soybean oil.

Embodiment B8. The composition for hair treatment according to any one of the preceding embodiments,
wherein the oxidation dye is separated and comprised in the first agent,
the oxidation initiator is in the second agent, and
the oil comprising olefin-based unsaturated hydrocarbon is in the third agent.

Embodiment B9. The composition for hair treatment according to any one of the preceding embodiments, wherein the first agent, the second agent and the third agent are mixed immediately before use and applied to hair.

Embodiment B10. The composition for hair treatment according to any one of the preceding embodiments, wherein the oxidation initiator facilitates a thiol-ene reaction between cysteine present in hair and the oil comprising olefin-based unsaturated hydrocarbon.

Embodiment B11. The composition for hair treatment according to any one of the preceding embodiments, wherein the composition for hair treatment has an effect of hair protection, hair recovery, giving condition feeling, prevention of hair oxidation, prevention of dye damage and color persistence.

Embodiment C1. A use for hair protection, hair recovery, giving condition feeling, prevention of hair oxidation, prevention of dye damage and hair color retention of the composition according to any one of the preceding embodiments.

Embodiment C2. A method for hair protection, hair recovery, giving condition feeling, prevention of hair oxidation, prevention of dye damage and hair color retention, comprising applying the composition according to any one of the preceding embodiments to a subject.

Embodiment C3. An application of the composition according to any one of the preceding embodiments for preparation of a hair product for hair protection, hair recovery, giving condition feeling, prevention of hair oxidation, prevention of dye damage and hair color retention.

Technical Solution

The technology in the present disclosure supplies an oil comprising olefin-based unsaturated hydrocarbon to damaged hair or protein-based fiber, to cause a thiol-ene reaction between a thiol group of cysteine present in the damaged hair or protein-based fiber and unsaturated group, thereby recovering damage and enhancing smoothness and gloss conditioning feeling. As described above, the reaction of improving hair and protein-based fiber by attaching a lipid component to cysteine can be promoted by using a metal catalyst and/or an oxidation initiator.

Part I. Composition for Hair Treatment Using Metal Catalyst

One aspect of the present disclosure is to provide a composition for hair treatment, comprising a transition metal catalyst and an oil comprising olefin-based unsaturated hydrocarbon.

The addition of a transition metal catalyst is contraindicated in hair cosmetics, because, in particular, it binds with lipids to form insoluble salts and supplies so-called scale, thereby causing side-effects of increasing hair stiffness, but in the present technology, the transition metal ion is responsible for supplying electrons as radicals to the thiol-ene reaction, and the olefin bound to the hair cysteine provides a large amount of continuous smoothness, and therefore, the metal catalyst rather produces an effect of increasing smoothness.

As one aspect of the present disclosure to solve the above problem, the present disclosure provides a bond allowing to have Chemical formula 1 below.

A-Z—R'  [Chemical formula 1]

In the Chemical formula 1, Z is an unsaturated bond linking group, and A is a functional group capable of forming a covalent bond in hair, and herein, in the Z which activates the thiol-ene reaction by binding an olefin linking group to the damaged hair, R' is a C1-22 alkyl group, or an ionizable functional group.

As above, M is a metal transition metal, and acts as a catalyst in the thiol-ene reaction.

Cysteine gives rough conditioning feeling to hair and reduces gloss, thereby dramatically increasing hair damage experience level. When oil is penetrated inside the hair or adhered outside, the conditioning feeling to hair may be increased, but there is a limit to providing a temporary effect, as it is removed during a cleaning and rinsing process.

As the transition metal catalyst, as monovalent, there may be Cu(I) iodie, Cu(I)oxide, Cu(I) chloride, Cu(I) bromide, Copper(I) cyanide, Copper(I) acetate, Copper(II) oxide, Copper(II) chloride, Copper(II) sulfate (CuSO$_4$), and the like. As divalent, there may be Copper(II) acetate, Copper (II) bromide, Copper(II) trifluoromethanesulfonate, Copper (II) fluoride, Copper(II) sulfide, Copper(II) acetylacetonate, Copper(II) acetate monohydrate, Copper(II) nitrate trihydrate, Copper(II) phthalocyanine, Copper(II) hydroxide, Copper(II) carbonate basic, Copper(II) 2-ethylhexanoate, Copper(II) hexafluoroacetylacetonate hydrate, and the like. As trivalent, there may be Iron (III) oxide, Iron (III) citrate, Iron (III) chloride, Iron (III) acetylacetonate, Iron (III) oxide, Iron (III) nitrate nonahydrate, Iron (III) tartrate, Iron (III) sulfate hydrate, Iron (III) trifluoromethanesulfonate, Iron (III) pyrophosphate, Iron (III) ferrocyanide, Iron (III) bromide, Iron (III) perchlorate hydrate, Iron (III) ionophore IV, Iron (III) phosphate dehydrate, Iron (III) oxalate hexahydrate, Iron (III) citrate tribasic monohydrate, Iron (III) p-toluenesulfonate hexahydrate, Iron (III) phosphate tetrahydrate, Iron (III) fluoride, Iron (III) phthalocyanine chloride, Iron (III) arsenide, Iron (III) nitrate, Iron (III) fluoride trihydrate, and the like, but not limited thereto.

The composition of the present disclosure contains an oil comprising olefin-based unsaturated hydrocarbon used in use for exhibiting gloss to hair or use for moisturizing. The oil is an olefin-based unsaturated hydrocarbon, and for example, it may comprise a C6~C22 fatty acid comprising one or more unsaturated groups. In addition, any oil that can change the conditioning feeling in hair by adsorbing or penetrating into the hair may be used without limitation.

As a non-limitative example of the oil, water-insoluble and non-volatile components commonly referred to as silicone such as dimethicone, cyclomethicone, aminated silicone, trimethylsilylamodimethicone or vinyl silicone, and derivatives thereof, and vegetable oil such as jojoba oil, vegetable fat and oil, animal oil, animal fat and oil, hydrocarbon oil or synthetic ester oil, or the like may be used. As the hydrocarbon oil, liquid paraffin, isoparaffin, or hydrogenated polydecene, or the like may be used, and as the ester oil, isopropyl myristate, isopropyl palmitate, isostearyl isostearate or C12~15 alkyl benzoate, triethylhexanoin, squalene, palm oil, Olea europaea oil, PPG-3 caprylyl ether, capric/caprylic triglyceride, isostearyl isostearate, coconut (*Cocos Nucifera*), polyglyceryl-6, octacaprylate, hydrogenated polydecene, jojoba seed (*Simmondsia Chinensis* seed) oil, DI-C 12-13 alkyl marate, or the like may be used, but not limited thereto.

The oil comprising olefin-based unsaturated hydrocarbon may preferably comprise unsaturated fatty acids of 50% by weight or more. This example includes olive oil, macadamia oil, jojoba oil, meadowfoam oil, argan oil, camelia oil, grape seed oil, sunflower oil, avocado oil, canola oil, corn oil, cottonseed oil, hempseed oil, flaxseed oil, linseed oil, palm oil, peanut oil, safflower oil and soybean oil, and the like, but not limited thereto.

In addition, the oil may be comprised by 0.05 to 10% by weight, specifically, 0.1 to 6% by weight, but not limited thereto.

The composition of the present disclosure as above may have an effect of hair protection, hair recovery, giving conditioning feeling or prevention of hair oxidation, and may be used for protection of protein-based fiber other than hair. In the composition for fiber treatment, the transition metal catalyst may give an effect of protection of protein-based fiber (for example, animal-derived natural fiber, protein regeneration artificial fiber, etc.) and damage recovery, by playing a role of promoting a thiol-ene reaction between cysteine present in the protein-based fiber and the olefin-based unsaturated hydrocarbon, by the same principle as aforementioned for the composition for hair treatment.

The composition for hair treatment of the present disclosure may further comprise any one or more selected from the group consisting of fat substances, organic solvents, dissolving agents, concentrates, gelling agents, anti-oxidants, suspending agents, solubilizers, foaming agents, flavoring agents, surfactants, water, ionic or non-ionic emulsifiers, filling agents, metal ion blocking agents, preservatives, vitamins, blocking agents, wetting agents, essential oil, dyes, pigments, hydrophilic or lipophilic activators, and the like, commonly used in hair products.

In addition, the composition of the present disclosure may further comprise an additive providing beneficial properties to the human body. For example, it may further comprise additives giving beneficial properties to the human body such as cleaning, volume, tidying, protection, blocking, moisturizing, dyeing, coloring, discoloration, restriction, deodorization, preservation, refreshing, hair removal, hair growth, anti-dandruff, hair loss prevention, hair growth, anti-inflammation, fragrance, flavoring, whitening, anti-aging, wrinkle improvement, convergence, relaxation, contraction, sebum suppression, keratin exfoliation, sterilization, anti-inflammation, anti-pruritic, deodorization, anti-histamine, anti-diarrheal, blood circulation promotion, ultraviolet protection or skin metabolism promotion, and the like.

In addition, the composition of the present disclosure may further contain a preservative, a thickener, a viscosity adjusting agent, a pH adjusting agent, a flavoring agent, a dye or a condition agent, which may be used as a component of a composition for hair, and they may be purchased commercially easily and used. The example of the preservative may include benzoic acid and salts, methyl paraoxybenzoate, a mixture of methylchloroisothiazolinone or methylisothiazolinone (product name: Kathon CG, manufacturer: The Dow Chemical Company), and the like. As the thickener and viscosity adjusting agent, hydroxypropylmethylcellulose, hydroxymethylcellulose, sodium chloride, ammonium chloride, propylene glycol, hexylene glycol, sodium xylene sulfonate, or ammonium xylene sulfonate, or the like may be used. As the pH adjusting agent, citric acid, sodium hydroxide or triethanolamine, or the like may be used. As the dye, water-soluble tar color may be used. Also, as the conditioning agent, animal and plant extract, protein and protein variants, higher fatty acid, and the like may be used.

The composition of the present disclosure may be prepared in a general emulsion formulation or solubilization formulation. In addition, the composition of the present disclosure may be prepared in all formulations capable of being applied to scalp such as liquid, cream, paste or solid, or the like.

Furthermore, the present disclosure provides a hair product comprising the composition for hair treatment, and the hair product may be selected from the group consisting of bleaching agents, dyeing agents, perm agents, hair treatment agents, hair clinic agents, hair nutrition agents, hair care agents, hair cleaning agents, shampoos, conditioners, hair tonics, hair conditioners, hair lotions, hair gels, hair packs, hair cream, hair essence, hair powder, hair spray, hair oil, hair styling agents, patches, spray and post-dye treatment agents, but not limited thereto.

Part II. Composition for Hair Treatment Using Oxidation Initiator

Other aspect of the present disclosure provides a composition for hair treatment comprising (i) an oxidation initiator and (ii) an oil comprising olefin-based unsaturated hydrocarbon.

When an oxidation hair dye or bleaching agent is used, there is a problem that hair damage and color loss occur easily, as the hair protection lipid layer on the hair surface is hydrolyzed by more than 50~70% with just one dye. In the past, technology to improve damage and color persistence by temporarily coating lipid-damaged parts, by applying silicone, cationic polymer, or the like has been introduced, but it was a situation in need of improvement due to lack of persistence by simple adsorption or ionic bonding.

Therefore, the present disclosure provides a composition for hair treatment capable of improving a problem of hair damage and deterioration of color persistence by oxidation dyeing and bleaching, by improving damaged hair lipid recovery and water resistance by covalently boding an alternative lipid component through a thiol-ene reaction to a thiol group generated after hair lipid damage.

The oxidation initiator comprised in the composition for hair treatment of the present disclosure is an initiator which promotes oxidation and decolorization of dye, and initiates a covalent bond of a keratin residue of hair and natural oil or derivatives thereof, and comprises an oxidation initiator components promoting at least one or more reactions, and for example, it means a component promoting an oxidation initiating reaction such as hydrogen peroxide, sodium perborate, sodium percarbonate, ammonium persulfate, bis maleimidoethoxy ethane, calcium peroxide, ferric chloride, hypochlorous acid, laccase, magnesium peroxide, MEK (methyl ethyl ketone) peroxide, melanin peroxide, ozonized turpentine, phthalimidoperoxycaproic acid, potassium bromate, potassium caroate, potassium chlorate, potassium monopersulfate, potassium persulfate, PVP-hydrogen peroxide, sodium bromate, sodium carbonate peroxide, sodium iodate, sodium perborate, sodium persulfate, strontium peroxide, urea peroxide and zinc peroxide.

The oil comprising olefin-based unsaturated hydrocarbon comprised in the composition for hair treatment of the present disclosure is same as described in the Part I. Preferably, the natural oil having a unsaturated double bond group used in the present disclosure has one or more unsaturated groups such as palmitoleic, oleic, linoleic, linolenic, gadoleic (11-eicosanoic), and nervonic groups, and it is preferable to use the composition of the unsaturated oil groups of 50% or more of the total oil composition.

As the natural oil comprising unsaturated fatty acids of 50% by weight or more and derivatives thereof, for example, one or more selected from the group consisting of olive oil, macadamia oil, jojoba oil, meadowfoam oil, argan oil, camelia oil, grape seed oil, sunflower oil, avocado oil, canola oil, corn oil, cottonseed oil, hempseed oil, flaxseed oil, linseed oil, palm oil, peanut oil, safflower oil and soybean oil may be used, but not limited thereto.

It is more preferable that the content of the oil component contains 0.5~5.0% of the total hair dye composition, and it is more preferable that the content of the oxidation initiator contains 0.1~15%.

The composition for hair treatment of the present disclosure may further additionally use an oxidation dye, and a specific example thereof may be one or more selected from the group consisting of phenylene diamine, aminophenol, resorcinol, aminocresol, methylhydroxyethylaminophenol, nitrophenylene diamine and toluene diamine sulfate, and specifically, paraphenylene diamine, methaphenylene diamine, metha-aminophenol, toluene-2,5-diamine sulfate, para-aminophenol, nitroparaphenylene diamine, para-amino-orthocresol and resorcinol, and the like may be used.

The composition for hair treatment of the present disclosure may consist of 2 agents or more, and the oxidation initiator and an oil comprising olefin-based unsaturated hydrocarbon may be comprised in different agents each other, respectively.

As a preferable embodiment, the oxidation initiator in the first agent, and the oil comprising olefin-based unsaturated hydrocarbon in the second agent may be separated and comprised, respectively, and they may be applied to hair by mixing them immediately before use.

In addition, in a preferable embodiment of the present disclosure, the oxidation dye in the first agent, the oxidation initiator in the second agent, and the oil comprising olefin-based unsaturated hydrocarbon in the third agent may be separated and comprised, respectively, and they may be applied to hair by mixing them immediately before use.

As one example, a product for hair treatment comprising the first agent, the second agent and the third agent comprising each of the components. More preferably, the product for hair treatment may be a product for hair dyeing or bleaching, and more preferably, it may be a product for hair dyeing.

As one example, a product for hair treatment consisting of the first agent, the second agent and the third agent comprising each of the components. More preferably, the product for hair treatment may be a product for hair dyeing or bleaching, and more preferably, it may be a product for hair dyeing.

The present inventors have found that in case of oil having many unsaturated groups, loss of the unsaturated groups occurs by hydrolysis under an alkali condition, and when it is mixed with hydrogen peroxide, the reaction is initiated by oxygen radicals, and the reactivity is lost when comprised in the formulation, and therefore, it cannot form a covalent bond, and thus it should be mixed and used right before use of a hair dye.

The composition for hair treatment comprising an oxidation initiator of the present disclosure as above has one or more effects selected from the group consisting of effects of hair protection, hair recovery, giving conditioning feeling, prevention of hair oxidation, prevention of dye damage and color persistence.

The composition for hair treatment according to the p resent invention may contain a component generally comprised in a hair dye and a bleaching agent, and the like, in addition to the above components. For example, it is not limited thereto, but it may contain a metal sequestering agent, a solvent, a surfactant, a thickener and a flavoring agent, and the like.

In addition, the composition for hair treatment according to the present disclosure is not limited thereto, but may be applied as a formulation of powder, paste, cream, lotion, gel, foam, aerosol or liquid.

[Effects]

The present disclosure has an effect of excellently increasing continuous hair protection and conditioning feeling by semi-permanently binding olefin oil to cysteine present in damaged hair or protein-based fiber through a thiol-ene reaction.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

MODE FOR INVENTION

Hereinafter, the present disclosure will be described in more detail through examples. These examples are intended only to describe the present disclosure more specifically, and it will be obvious to those skilled in the art to which the present disclosure pertains that the scope of the present disclosure is not limited by these examples.

Materials and reagents used in the present experimental example were purchased from cosmetic raw material manufacturers and commercial suppliers and used.

Experimental Example

I. Composition for Hair Treatment Comprising a Metal Catalyst

1. Preparation of a Bleaching Agent

TABLE 1

| Use | Mixing component | Weight ratio (%) |
| --- | --- | --- |
| First agent | Ammonia water 28% | 4 |
| | MEA | 8 |
| | Purified water | Residual (to 100) |
| Second agent | Hydrogen peroxide | 17 |
| | Turpinal SL | 0.17 |
| | Olefin-based unsaturated hydrocarbon | 4 |
| | Metal catalyst | 0.4 |
| | Purified water | Residual (to 100) |

A bleaching agent was prepared as Table 1. To the second agent of this bleaching agent, an oil comprising olefin-based unsaturated hydrocarbon of 4% was added, and a metal catalyst of 0.4% which was 10% thereof was added.

Treatment of the bleaching agent at twice of the hair weight was performed to a 1 g hair tress for 20 minutes (which is a normal bleaching treatment time), and then it was rinsed with running water at a flow rate of 4 ml/sec for 5 minutes.

2. Evaluation of Smoothness Upon Addition According to the Number of Transition Metal Catalyst Ions

TABLE 2

| Experiment | Comparative example I-1 | Comparative example I-2 | Example I-1 | Example I-2 | Example I-3 | Example I-4 | Example I-5 | Example I-6 | Example I-7 | Comparative example I-3 | Comparative example I-4 |
|---|---|---|---|---|---|---|---|---|---|---|---|
| Olefin | — | Olive oil | Olive oil | Olive oil | Olive oil | Olive oil | Olive oil | Olive oil | Olive oil | Olive oil | Olive oil |
| Metal catalyst | | | Cu(I) bromide | Cu(I) chloride | Cu(I) Iodide | Cu(II) sulfate | Cu(II) bromide | Cu(II) chloride | Fe(II) chloride | Fe(III) bromide | Fe(III) chloride |

As Table 2, Cu and Fe were used and selected as a transition metal catalyst comprised in the second agent of Table 1. As mentioned as the example above, many types of transition metal catalysts exist depending on the counter ion, but bromide and chloride, and iodide were limitedly selected to compare the role of the metal catalysts under conditions of equal chemical binding force. Since a trivalent Cu compound does not exist, with an element having the same counter ion used as Cu in the monovalent and divalent experiments, experiments were performed using Fe.

However, as defined in Table 3, as iodide which was Example I-2 in the monovalent ion experiment showed a similar result with chloride which was Example I-3, the counter ion compound of iodide was excluded in the divalent and trivalent samples in the present experiment.

Comparative example I-1 is damaged hair, and Comparative example I-2 is hair containing olefin. Comparative example I-2 was washed for 5 minutes after applying olefin to twice the hair weight.

For the degree of smoothness of the present experimental samples, the friction force was evaluated using MTT 175 Miniature Tensile Tester (DiaSTRON, GB). After rinsing the treated hair for a few minutes, it was dried with a dryer for 2 minutes, and it was maintained at 25° C. in a constant temperature and humidity room with a humidity of 50% for one day, and the moisture inside the hair was made constant, respectively, and then the friction force was measured in the constant temperature and humidity room and the result was shown in Table 3 below.

Then, the hair tress was washed with sodium lauryl sulfate, an anionic surfactant, and then the change in the hair surface friction force (%) was calculated as Table 3 by comparing the difference value with the corresponding measured value using this as a reference value. The larger the value, the larger the friction force change value, which reflected the increase smoothness.

From the result of Table 3, it can be seen that the friction force, which is inversely proportional to the smoothness, is significantly changed and decreased, when modification is made to monovalent or divalent. On the other hand, it can be seen that as Example I-7, Fe obviously reduced the friction force, but as shown in Comparative samples I-3 and I-4, when a trivalent metal catalyst acted, a group bound to fatty acid acted more on the hair, so it had no effect on reducing the friction force. This is because the activation energy of the trivalent radical ion as a catalyst acting on thiol-ene is high and therefore, it does not affect hair cysteine. In addition, it can be seen that it has a rougher surface than Comparative example I-2 without a metal catalyst due to unique metallic feeling of Fe.

On the other hand, referring to Example I-4, it can be seen that there is a difference in the effect of preventing surface damage depending on the counter ion, even if the same metal ion is a divalent ion. This is because the thiol-ene radical reaction was not promoted as the charge density was relatively low when the counter ion was sulfate, which is hexavalent. Br or Cl series having relatively high charge density are most suitable as a metal catalyst because they sufficiently perform a radical reaction.

Comparative example I-2 shows friction force similar to that of Example I-4, so it may seem that there is no need for a metal catalyst. However, this is a temporary rather than semi-permanent effect, and it had a conditioning effect due to the oily feeling right after applying oil, but since there was no binding to hair, the oil was washed away after washing, eventually reaching the same value as Comparative example I-1. In order to obtain a high friction force change value only by olefin treatment, an excess of olefin treatment was required than twice the hair weight, and since even this was removed by repeated washing, it was confirmed that this was only a temporary effect.

Finally, as the result of changing the content by selecting Cu(II) Chloride, which had the best smoothness conditioning effect, it was confirmed that the present metal catalyst had the best efficacy when it was 1% to 15% compared to olefin.

3. Pretreatment Agent Preparation and Effect Evaluation

In the process of bleaching the hair, a metal catalyst was added to the hair. As shown in Table 4 below, before bleaching, that is, before treatment with a bleaching agent, a bleaching pretreatment agent treating a metal catalyst to hair was prepared, and to examine when it was effective to treat the metal catalyst.

TABLE 3

| Comparative example I-1 | Comparative example I-2 | Example I-1 | Example I-2 | Example I-3 | Example I-4 | Example I-5 | Example I-6 | Example I-7 | Comparative example I-3 | Comparative example I-4 |
|---|---|---|---|---|---|---|---|---|---|---|
| 0 | 6 | 11 | 14 | 14 | 6 | 21 | 24 | 20 | 4 | 4 |

TABLE 4

| Use | Mixing component | Weight ratio (%) |
|---|---|---|
| Pretreatment agent | Olive oil | 4 |
| | Metal catalyst | 0.4 |
| | Purified water | Residual (to 100) |

As the metal catalyst comprised in the pretreatment agent, those described in Table 5 below were used. As such, pretreatment agents 1~8 comprising the metal catalyst with double bond olive oil were prepared, and before using a bleaching agent, which is a peroxide-based hair cosmetic, the degree of smoothness was evaluated through the change in the friction force on the hair surface according to single use of them, and the result was shown in Table 5 below.

TABLE 5

| Experiment | Pretreatment agent 1 | Pretreatment agent 2 | Pretreatment agent 3 | Pretreatment agent 4 | Pretreatment agent 5 | Pretreatment agent 6 | Pretreatment agent 7 | Pretreatment agent 8 |
|---|---|---|---|---|---|---|---|---|
| Metal catalyst | Cu(I) bromide | Cu(I) chloride | Cu(I) Iodide | Cu(II) bromide | Cu(II) chloride | Fe(II) chloride | Fe(III) bromide | Fe(III) chloride |
| Friction force change(%) | 2 | 3 | 3 | 3 | 2 | 3 | 3 | <0 |

As can be seen in Table 5, it can be seen that when a metal catalyst is pretreated with a double bond group before using a bleaching agent which is a hydroxide-based hair cosmetic, there is no effect in enhancing a thiol-ene reaction. When olive oil or oil is adhered alone, it penetrates due to hydrophobic binding with protein inside hair as studied in the document [Ruetsch, S. B.; Kamath, Y. K.; Rele, A. S.; Mohile, R. B., Secondary ion mass spectrometric investigation of penetration of coconut and mineral oils into human hair fibers: Relevance to hair damage. Journal of Cosmetic Science 2001, 52 (3), 169-184.]. the pretreatment appears to be ineffective as this induces separation from the metal catalyst. Therefore, it can be seen that the metal catalyst is used together with an oxidizing agent, and when the disulfide of the hair is damaged, the thiol-ene reaction should be given immediately.

4. Evaluation of Effect Using Alkali Earth Metal Catalyst

The effect was evaluated using the alkali earth metal catalyst shown in Table 6 below as the metal catalyst comprised in the second agent of Table 1 above. A thiol-ene reaction was caused by one-time use of the bleaching agent comprising the alkali earth metal catalyst, and the reactivity was evaluated by a rate of change in hair surface friction force (%) and shown in Table 6 below.

TABLE 6

| Metal catalyst | Beryllium | Magnesium | Calcium | Strontium |
|---|---|---|---|---|
| Change in friction force (%) | 2 | 3 | 3 | 3 |

As the result of the experiment, when using the alkali earth metal as a metal catalyst, as Table 6 above, there was no reaction at all. This is because the radical reaction is difficult as electrons are filled up to the s or f orbital in case of the alkali earth metal, whereas the radical reaction is easy to occur as electrons are filled up to the d orbital in case of Cu or Fe, and this promotes the thiol-ene reaction as a metal catalyst.

5. Evaluation of Gloss Value, Flexural Strength, and Combing Strength

In Table 7, gloss was measured by L=100*Sin/S_out*1/W_visual using colorimeter Samba (Samba, Bossa Nova Vision, Fr), and S is the amount of reflection and W is the width (angle) of the measurement range.

In Table 7, in order to evaluate the rigidity of hair, it was evaluated by using a flexural strength estimator KES-FB2-S (KATO TECH, Japan).

In Table 7, for the combing strength, the friction force applied during the combing test was evaluated by using MTT 175 Miniature Tensile Tester (DiaSTRONG, GB). It means that as the value increases, the force applied to the comb increases, meaning that the hair is tangled.

The Examples and Comparative examples of Table 7 mark physical property values of hairs treated with a metal catalyst in the pretreatment agent as Table 5. Comparative example I-5 is non-treated, and Comparative I-6 contains only olefin. Example I-8 and Example I-9 are treated with a pretreatment agent containing Cu(I) Chloride and Cu(II) Chloride with olefin, and Comparative example I-7 is a physical property value experimented with hair treated with the pretreatment agent containing Fe(III) Chloride.

TABLE 7

| Sample | Comparative example I-5 | Comparative example I-6 | Example I-8 | Example I-9 | Comparative example I-7 |
|---|---|---|---|---|---|
| Gloss value | 12 | 16 | 32 | 37 | 11 |
| Flexural strength (gf * cm) | 0.46 | 0.45 | 0.83 | 0.94 | 0.45 |
| Combing strength (J) | $2.73 \times 10^{-1}$ | $1.03 \times 10^{-1}$ | $4.24 \times 10^{-2}$ | $3.28 \times 10^{-2}$ | $2.15 \times 10^{-1}$ |

In Examples 7 and 8, it can be seen that as the gloss value increases, the flexural strength value increases and the combing strength value also decreases. As can be seen from the above device evaluation, it was confirmed that the monovalent and divalent metal catalyst radicals added in the present disclosure completed the thiol bond of olefin through a catalytic reaction, thereby significantly increasing the conditioning feeling.

6. Evaluation of Degree of Damage Inside the Hair when Using Hair Dye

Finally, in order to evaluate the degree of damage inside the hair when using a hair dye, based on documents [Ryu, S. R.; Jang, W.; Yu, S. I.; Lee, B. H.; Kwon, O. S.; Shin, K., FT-IR Microspectroscopic Imaging of Cross-Sectioned Human Hair during a Bleaching Process. J. Cosmet. Dermatol. Sci. Appl. 2016, 6 (5), 181-190.], a hair section specimen was produced, and the cysteine monoxide produced when hair damage occurs was measured at 1072 $cm^{-1}$ to perform IR mapping. Normalization was conducted by taking Amide I as a reference point, and the resulting image of the degree of damage on the hair section was shown in FIG. 2.

Figure 1:
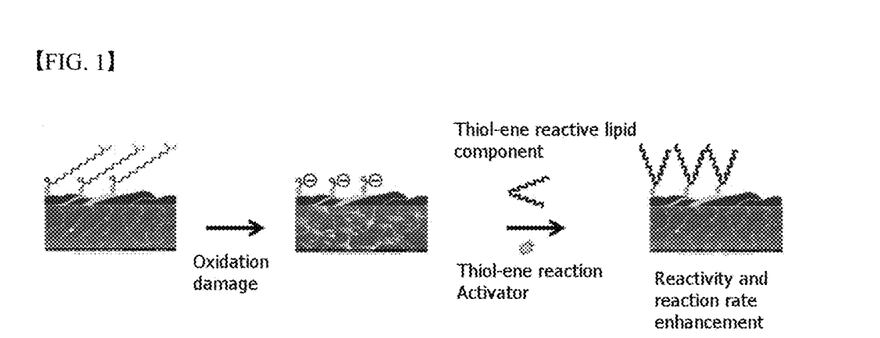
FIG. 1 schematizes the process in which oxidatively damaged hair is recovered through a reaction between olefin oil and thiolene.
Figure 2:
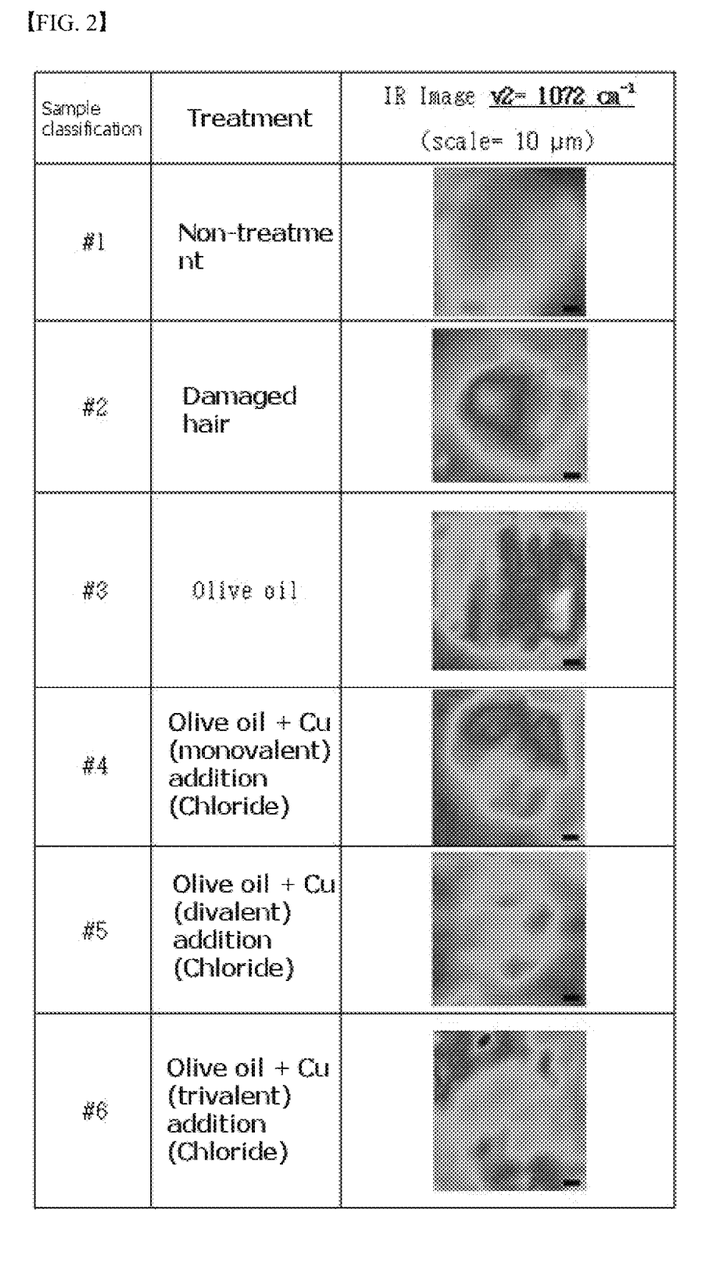
FIG. 2 shows an image of a hair cross-section damage degree.

In FIG. 2, the color strength of 1072 $cm^{-1}$ of the wavenumber (green: high, blue: low) represents the degree of damage. Only the #1 result image is non-treatment hair, and from #2, oxidative damage is progressed with hair dye. The circle in the figure indicates the hair section.

As shown in the result of FIG. 2, it can be seen that damage inside the hair was dramatically prevented in the process of dyeing and bleaching or perm oxidation damage, when a divalent copper ion was used as a chloride counter ion as #5.

II. Composition for Hair Treatment Comprising Oxidation Initiator

1. Case of Directly Mixing and Applying Oil to Hair Dye

The case of directly mixing and applying natural oil having the composition of the unsaturated group of 50% or more and an oil derivative was prepared as a comparative example.

Specifically, the first oxidation hair dye agent was prepared by heating purified water to 70° C., and then sequentially adding each component, stirring, dissolving and cooling to 50° C. or less, and then adding monoethanol and subsequent components. The second agent was prepared by heating purified water to 70° C. and then sequentially adding each component, stirring, dissolving and cooling to 45° C. or less, and adding hydrogen peroxide and stirring.

Table 8 below presents the first oxidation hair dye agent and Table 9 represents the second oxidation hair dye agent.

TABLE 8

| Classification (% by weight) | Comparative example II-1-1 | Comparative example II-1-2 | Comparative example II-1-3 | Comparative example II-1-4 | Comparative example II-1-5 | Comparative example II-1-6 |
|---|---|---|---|---|---|---|
| Purified water | Up to 100 % by weight | | | | | |
| EDTA·4Na | 0.2 | 0.2 | 0.2 | 0.2 | 0.2 | 0.2 |
| Propylene glycol | 3.00 | 3.00 | 3.00 | 3.00 | 3.00 | 3.00 |
| Sodium sulfite | 0.70 | 0.70 | 0.70 | 0.70 | 0.70 | 0.70 |
| Cetyl alcohol | 4.00 | 4.00 | 4.00 | 4.00 | 4.00 | 4.00 |
| Stearyl alcohol | 2.00 | 2.00 | 2.00 | 2.00 | 2.00 | 2.00 |
| Steatrimonium chloride | 2.50 | 2.50 | 2.50 | 2.50 | 2.50 | 2.50 |
| Polyoxyethylene cetyl ether | 2.50 | 2.50 | 3.50 | 2.50 | 3.50 | 3.50 |
| p-phenylene diamine | 0.900 | 0.900 | 0.900 | 0.900 | 0.900 | 0.900 |
| m-aminophenol | 0.300 | 0.300 | 0.300 | 0.300 | 0.300 | 0.300 |
| Resorcinol | 1.050 | 1.050 | 1.050 | 1.050 | 1.050 | 1.050 |
| p-aminophenol | 0.300 | 0.300 | 0.300 | 0.300 | 0.300 | 0.300 |
| p-amino-o-cresol | 0.015 | 0.015 | 0.015 | 0.015 | 0.015 | 0.015 |
| 2-methyl-5-hydroxyethyl aminophenol | 0.005 | 0.005 | 0.005 | 0.005 | 0.005 | 0.005 |
| Monoethanol amine | 6.00 | 6.00 | 6.00 | 6.00 | 6.00 | 6.00 |
| Polyquaternium-7 | 0.2 | 0.2 | 0.2 | 0.2 | 0.2 | 0.2 |
| Olive oil | 2.0 | | | | | |
| Meadowfoam oil | | 2.0 | | | | |
| Argan oil | | | 2.0 | | | |
| No oil | | | | — | | |
| Coconut oil | | | | | 2.0 | |
| Hydrogenated palm oil | | | | | | 2.0 |
| pH | 10.3 | 10.4 | 10.4 | 10.5 | 10.4 | 10.2 |

TABLE 9

| Component | Comparative example |
|---|---|
| Purified water | Up to 100% by weight |
| Cetostearyl alcohol | 3.00 |
| Polyoxyethylene lauryl ether | 0.80 |
| Etidronic acid | 0.10 |
| Phosphoric acid | 0.10 |
| Sodium monohydrogen phosphate | 0.20 |
| Hydrogen peroxide solution | 6.0 |
| pH | 3.3 |

After mixing the first agent of Table 8 and the second agent of Table 9 prepared as above at 1:1 well, it was applied to the hair and it was left for 30 minutes, and then it was washed, and thereby, dyeing was conducted.

(1) Friction Coefficient Measurement

The dyed hair was fixed to an acryl tress by 4 g, and then it was measured using a tensile strength measuring instrument (MTT 175) and the result was shown in Table 10 below. It means that the smaller the value, the smoother the surface.

TABLE 10

| | Friction Coefficient | | | | | |
|---|---|---|---|---|---|---|
| Evaluation sample | Comparative example II-1-1 | Comparative example II-1-2 | Comparative example II-1-3 | Comparative example II-1-4 | Comparative example II-1-5 | Comparative example II-1-6 |
| Friction Coefficient | 0.65 | 0.66 | 0.67 | 0.74 | 0.66 | 0.68 |

(2) Measurement of Combing Force

The dyed hair was fixed to an acryl tress by 4 g, and then it was measured using a tensile strength measuring instrument (MTT 175) and the result was shown in Table 11 below. It means that the smaller the value, the easier combing of the hair without tangling.

TABLE 11

| | Combing Force(mJ) | | | | | |
|---|---|---|---|---|---|---|
| Evaluation sample | Comparative example II-1-1 | Comparative example II-1-2 | Comparative example II-1-3 | Comparative example II-1-4 | Comparative example II-1-5 | Comparative example II-1-6 |
| Combing Force | 63 | 66 | 64 | 73 | 68 | 67 |

(3) Comparative Experiment of Water Loss after Shampoo

SLES 6% solution was applied to the dyed hair as much as ¹/₁₀ of the sample weight, and then it was repeatedly washed under the same condition. During washing, the flow rate was 30 ml/s, and a total of 28 washes were performed assuming 15 seconds of foaming, 40 seconds of massage, 60 seconds of cleaning and 4 weeks of cleaning. The experimental result of measuring the ΔE value was shown in Table 12 below. It means that the smaller the ΔE value, the less the change in the water loss color.

TABLE 12

| | Water loss test (ΔE) | | | | | |
|---|---|---|---|---|---|---|
| Evaluation sample | Comparative example II-1-1 | Comparative example II-1-2 | Comparative example II-1-3 | Comparative example II-1-4 | Comparative example II-1-5 | Comparative example II-1-6 |
| Color change | 1.85 | 1.71 | 1.84 | 2.10 | 2.01 | 2.03 |

(4) Panel Evaluation of Hair Damage after Dyeing

The dyed hair was evaluated by giving a higher score as 15 professional panels felt less damage through touch evaluation such as hand combing, softness, and the like, and the result was shown in Table 13 below. It was evaluated based on a 5-point scale, and it means that the smaller the value, the easier it was to comb the hair without tangling.

TABLE 13

| | Conditioning feeling | | | | | |
|---|---|---|---|---|---|---|
| Evaluation sample | Comparative example II-1-1 | Comparative example II-1-2 | Comparative example II-1-3 | Comparative example II-1-4 | Comparative example II-1-5 | Comparative example II-1-6 |
| Evaluation score | 3.3 | 3.4 | 3.2 | 2.3 | 3.4 | 3.1 |

2. Case of Preparing Hair Dye, Oxidation Initiator and Oil Separately and Mixing and Applying Immediately Before Use The case of preparing a hair dye, an oxidation initiator and oil separately and mixing them immediately before use was prepared as described in Tables 14~16. Table 14 represents the first oxidation hair dye agent, and Table 15 represents the second oxidation hair dye agent, and Table 16 represents the third oil agent.

Specifically, the first oxidation hair dye agent was prepared by heating purified water to 70° C., and then sequentially adding each component, stirring, dissolving and cooling to 50° C. or less, and then adding monoethanol and subsequent components. The second agent was prepared by heating purified water to 70° C. and then sequentially adding each component, stirring, dissolving and cooling to 45° C. or less, and adding hydrogen peroxide and stirring.

TABLE 14

| Classification (% by weight) | Example and Comparative example |
|---|---|
| Purified water | Up to 100% by weight |
| EDTA·4Na | 0.2 |

TABLE 14-continued

| Classification (% by weight) | Example and Comparative example |
|---|---|
| Propylene glycol | 3.00 |
| Sodium sulfite | 0.70 |
| Cetyl alcohol | 4.00 |
| Stearyl alcohol | 2.00 |
| Steartrimonium chloride | 2.50 |
| Polyoxyethylene cetyl ether | 2.50 |
| p-phenylene diamine | 0.900 |
| m-aminophenol | 0.300 |
| Resorcinol | 1.050 |
| p-aminophenol | 0.300 |
| p-amino-o-cresol | 0.015 |
| 2-methyl-5-hydroxyethyl aminophenol | 0.005 |
| Monoethanol amine | 6.00 |
| pH | 10.3 |

TABLE 15

| Component | Example and Comparative example |
|---|---|
| Purified water | Up to 100% by weight |
| Cetostearyl alcohol | 3.00 |
| Polyoxyethylene lauryl ether | 0.80 |
| Etidronic acid | 0.10 |
| Phosphoric acid | 0.10 |
| Sodium monohydrogen phosphate | 0.20 |
| Hydrogen peroxide solution | 6.0 |
| pH | 3.3 |

TABLE 16

| Classification (% by weight) | Example II-1 | Example 11-2 | Example 11-3 | Comparative example II-2-1 | Comparative example II-2-2 | Comparative example II-2-3 |
|---|---|---|---|---|---|---|
| Olive oil | 2.0 | | | | | |
| Meadowfoam oil | | 2.0 | | | | |
| Argan oil | | | 2.0 | | | |
| No oil | | | | — | | |
| Coconut oil | | | | | 2.0 | |
| Hydrogenated palm oil | | | | | | 2.0 |

(2) Measurement of Combing Force

The dyed hair was fixed to an acryl tress by 4 g, and then it was measured using a tensile strength measuring instrument (MTT 175) and the result was shown in Table 18 below. It means that the smaller the value, the easier combing of the hair without tangling.

Test method, invention effect, and experimental result (Examples and Comparative examples 2-1~3)

After mixing the third agent of the comparative example to the first agent and the second agent prepared as above at 1:1 well, it was applied to the hair and it was left for 30 minutes, and then it was washed, and thereby, dyeing was conducted.

(1) Friction Coefficient Measurement

The dyed hair was fixed to an acryl tress by 4 g, and then it was measured using a tensile strength measuring instrument (MTT 175) and the result was shown in Table 17 below. It means that the smaller the value, the smoother the surface.

TABLE 17

| | Friction Coefficient | | | | | |
|---|---|---|---|---|---|---|
| Evaluation sample | Example II-1 | Example II-2 | Example II-3 | Comparative example II-2-1 | Comparative example II-2-2 | Comparative example II-2-3 |
| Friction Coefficient | 0.57 | 0.61 | 0.59 | 0.71 | 0.68 | 0.65 |

(2) Measurement of Combing Force

The dyed hair was fixed to an acryl tress by 4 g, and then it was measured using a tensile strength measuring instrument (MTT 175) and the result was shown in Table 18 below. It means that the smaller the value, the easier combing of the hair without tangling.

Test method, invention effect, and experimental result (Examples and Comparative examples 2-1~3)

After mixing the third agent of the comparative example to the first agent and the second agent prepared as above at 1:1 well, it was applied to the hair and it was left for 30 minutes, and then it was washed, and thereby, dyeing was conducted.

(1) Friction Coefficient Measurement

The dyed hair was fixed to an acryl tress by 4 g, and then it was measured using a tensile strength measuring instrument (MTT 175) and the result was shown in Table 17 below. It means that the smaller the value, the smoother the surface.

TABLE 18

| | Combing Force(mJ) | | | | | |
|---|---|---|---|---|---|---|
| Evaluation sample | Example II-1 | Example II-2 | Example II-3 | Comparative example II-2-1 | Comparative example II-2-2 | Comparative example II-2-3 |
| Combing Force | 48 | 45 | 50 | 73 | 68 | 67 |

(3) Comparative Experiment of Water Loss after Shampoo

SLES 6% solution was applied to the dyed hair as much as 1/10 of the sample weight, and then it was repeatedly washed under the same condition. During washing, the flow rate was 30 ml/s, and a total of 28 washes were performed assuming 15 seconds of foaming, 40 seconds of massage, 60 seconds of cleaning and 4 weeks of cleaning. The experimental result of measuring the $\Delta E$ value was shown in Table 19 below. It means that the smaller the $\Delta E$ value, the less the change in the water loss color.

TABLE 19

| | Water loss test ($\Delta E$) | | | | | |
|---|---|---|---|---|---|---|
| Evaluation sample | Example II-1 | Example II-2 | Example II-3 | Comparative example II-2-1 | Comparative example II-2-2 | Comparative example II-2-3 |
| Color change | 0.45 | 0.51 | 0.50 | 1.56 | 2.14 | 2.01 |

(4) Panel Evaluation of Hair Damage after Dyeing

The dyed hair was evaluated by giving a higher score as 15 professional panels felt less damage through touch evaluation such as hand combing, softness, and the like, and the result was shown in Table 20 below. It was evaluated based on a 5-point scale, and it means that the smaller the value, the easier it was to comb the hair without tangling.

TABLE 20

| | Conditioning feeling | | | | | |
|---|---|---|---|---|---|---|
| Evaluation sample | Example II-1 | Example II-2 | Example II-3 | Comparative example II-2-1 | Comparative example II-2-2 | Comparative example II-2-3 |
| Evaluation score | 4.1 | 3.8 | 3.9 | 2.5 | 3.2 | 3.3 | judging from the above result, it could be confirmed that a hair dye which applies natural oil that has at least one or more double bonds and has the composition of the unsaturated oil group of 50% or more or a derivative thereof to minimize hair damage and improves the color persistence after dyeing could be prepared.

3. Examples of Preferable Bleaching Agents According to the Present Disclosure

As one preferable example of the present disclosure, as described in Tables 21~23 below, bleaching agents were prepared. Table 21 shows the first bleaching agent, and Table 22 shows the second bleaching agent and Table 23 shows the third oil agent.

TABLE 21

| Classification (% by weight) | Content |
| --- | --- |
| Purified water | Up to 100% by weight |
| EDTA•4Na | 0.2 |
| Propylene glycol | 3.00 |
| Sodium sulfite | 0.70 |
| Cetyl alcohol | 4.00 |
| Stearyl alcohol | 2.00 |
| Steartrimonium chloride | 2.50 |
| Polyoxyethylene cetylether | 2.50 |
| Monoethanolamine | 6.00 |
| pH | 10.3 |

TABLE 22

| Component | Content |
| --- | --- |
| Purified water | Up to 100% by weight |
| Cetostearyl alcohol | 3.00 |
| Polyoxyethylene laurylether | 0.80 |
| Etidronic acid | 0.10 |
| Phosphoric acid | 0.10 |
| Sodium monohydrogen phosphate | 0.20 |
| Hydrogen peroxide solution | 6.0 |
| pH | 3.3 |

TABLE 23

| Classification (% by weight) | Content |
| --- | --- |
| Olive oil | 2.0 |

The invention claimed is:

1. A method for hair treatment comprising
applying a composition comprising: (i) an oxidation dye, (ii) an oxidation initiator, and (iii) an oil comprising olefin-based unsaturated hydrocarbon to a subject in need thereof,
wherein the oxidation dye is separate and contained in a first agent,
the oxidation initiator is separate and contained in a second agent, and
the oil comprising olefin-based unsaturated hydrocarbon is separate and contained in a third agent,
wherein the first agent, the second agent and the third agent are mixed immediately before use,
wherein the oxidation dye is one or more selected from the group consisting of phenylene diamine, aminophenol, resorcinol, aminocresol, methylhydroxyethylaminophenol, nitrophenylene diamine and toluene diamine sulfate,
wherein the oxidation initiator is one or more selected from the group consisting of hydrogen peroxide, calcium peroxide, magnesium peroxide, MEK (methyl ethyl ketone) peroxide, melanin peroxide, PVP-hydrogen peroxide, sodium carbonate peroxide, strontium peroxide, urea peroxide and zinc peroxide, and
wherein the oil comprising olefin-based unsaturated hydrocarbon is one or more selected from the group consisting of olive oil, meadowfoam oil, and argan oil.

2. The method for hair treatment according to claim 1, wherein the oxidation dye is one or more selected from the group consisting of phenylene diamine, aminophenol, resorcinol, aminocresol, methylhydroxyethylaminophenol, and toluene diamine sulfate.

3. The method for hair treatment according to claim 1, wherein the oxidation initiator further comprises one or more selected from the group consisting of sodium perborate, sodium percarbonate, ammonium persulfate, bis maleimidoethoxy ethane, ferric chloride, hypochlorous acid, laccase, melanin peroxide, ozonized turpentine, phthalimidoperoxycaproic acid, potassium bromate, potassium caroate, potassium chlorate, potassium monopersulfate, potassium persulfate, sodium bromate, sodium iodate, sodium perborate, and sodium persulfate.

4. The method for hair treatment according to claim 1, wherein the olefin-based unsaturated hydrocarbon is olive oil.

5. The method for hair treatment according to claim 1, wherein the oil comprising olefin-based unsaturated hydrocarbon comprises one or both of meadowfoam oil and argan oil.

6. The method for hair treatment according to claim 1, wherein the oil comprising olefin-based unsaturated hydrocarbon further comprises one or more selected from the group consisting of macadamia oil, jojoba oil, camelia oil, grape seed oil, sunflower oil, avocado oil, canola oil, corn oil, cottonseed oil, hempseed oil, flaxseed oil, linseed oil, palm oil, peanut oil, safflower oil and soybean oil.

7. The method for hair treatment according to claim 1, wherein the oxidation initiator facilitates a thiol-ene reaction between cysteine present in hair and the oil comprising olefin-based unsaturated hydrocarbon.

8. The method for hair treatment according to claim 1, wherein the composition for hair treatment has an effect of hair protection, hair recovery, giving condition feeling, prevention of hair oxidation, prevention of dye damage and color persistence.

9. The method for hair treatment according to claim 1, wherein the hair treatment provides a friction coefficient of 0.57-0.61.

10. The method for hair treatment according to claim 1, wherein the hair treatment provides a combing force of 45-50 mJ.

11. The method for hair treatment according to claim 1, wherein the hair treatment provides a water loss (ΔE) value of 0.45-0.51.

12. The method for hair treatment according to claim 1, wherein the hair treatment results in a lower fiction coefficient compared to a comparative composition that differs by not using an olefin-based unsaturated hydrocarbon comprising olive oil, meadowfoam oil, or argan oil.

13. The method for hair treatment according to claim 1, wherein the hair treatment results in a lower combing force compared to a comparative composition that differs by not using an olefin-based unsaturated hydrocarbon comprising olive oil, meadowfoam oil, or argan oil.

14. The method for hair treatment according to claim 1, wherein the hair treatment results in a lower water loss (ΔE) value compared to a comparative composition that differs by not using an olefin-based unsaturated hydrocarbon comprising olive oil, meadowfoam oil, or argan oil.

* * * * *